United States Patent [19]
Sackner et al.

[11] Patent Number: 5,159,935
[45] Date of Patent: Nov. 3, 1992

[54] NON-INVASIVE ESTIMATION OF INDIVIDUAL LUNG FUNCTION

[75] Inventors: Marvin A. Sackner, Miami Beach, Fla.; Joathan D. Sackner, New York, N.Y.

[73] Assignee: Nims, Inc., Miami Beach, Fla.

[21] Appl. No.: 491,675

[22] Filed: Mar. 8, 1990

[51] Int. Cl.⁵ .......................... A61B 5/08; A61B 5/113

[52] U.S. Cl. .................................... 128/721; 128/725

[58] Field of Search ...................... 128/716, 720–723, 128/725, 774, 782

[56] References Cited

U.S. PATENT DOCUMENTS

| | | | |
|---|---|---|---|
| 4,308,872 | 1/1982 | Watson et al. | 128/725 |
| 4,373,534 | 2/1983 | Watson | 128/725 |
| 4,452,252 | 6/1984 | Sackner | 128/721 |
| 4,572,197 | 2/1986 | Moore et al. | 128/721 |
| 4,777,962 | 10/1988 | Watson et al. | 128/721 |
| 4,807,640 | 2/1989 | Watson et al. | 128/721 |
| 4,815,473 | 3/1989 | Watson et al. | 128/721 |
| 4,817,625 | 4/1989 | Miles | 128/725 |
| 4,834,109 | 5/1989 | Watson | 128/721 |
| 4,960,118 | 10/1990 | Pennock | 128/721 |
| 4,966,155 | 10/1990 | Jackson | 128/721 |

OTHER PUBLICATIONS

Gaensler, E. A.: Bronchospirometry. I. Review of the Literature. J. Lab & Clin. Med. 39:917–934, 1952. Cited in the application on p. 1, lines 17–19; p. 5, lines 19–20; and p. 12, lines 17–19.

Ball, W. C. Jr., Stewart, P. B., Newsham, I. G. S., and Bates, D. V.: Regional pulmonary function studied with Xenon[133]. J. Clin. Invest. 4: 519–531, 1962. Cited in the application on p. 1, lines 26–28.

Gaensler, E. A., Patten, W. E. and Frank, N. R.: Bronchospirometry. VII. Indications. J. Lab. & Clin. Med. 41: 456–477, 1953. Cited in the application on p. 2, lines 25–26 and p. 7, lines 20–22.

Gaensler, E. A. and Watson, T. R. Jr.: Bronchospironmetry III. Complications, contraindications, technique and interpretation. J. Lab & Clin. Med. 40: 223–251, 1952, Cited in the application on p. 3, lines 1–3 and p. 7, lines 22–24.

Gaensler, E. A., Maloney, J. V., and Bjork, V. O.: Bronchospirometry. II. Experimental observations and theoretical considerations of resistance breathing. J. Lab & Clin Med. 39: 935–953, 1952. Cited in the application of p. 3, lines 3–6, 15–17, p. 4, lines 11–14, p. 5, line 24–p. 6, line. 2.

Wanner, A., and Sackner, M. A.: Transvenous phrenic nerve stimulation in anesthetized dogs. J. Appl. Physiol 34: 489–494, 1973. Cited in the application on p. 10, lines 20–22.

Rothstein, E., Strzelczyk, R.: Voluntary: Unilateral Breathing:. Am. Int. Med. 34: 401–406, 1951. Cited in the application on p. 12, lines 22–24 and p. 13, lines 5–6.

Sackner, M. A., Gonzalez, H., Rodriguez, M., Belsito, A., Sackner, D. R. and Grenvik, S.: Assessment of asynchronous and paradoxic motion between rib cage and abdomen in normal subjects and in patients with chronic obstructive pulmonary disease. A. Rev. Respir. Dis. 130: 588–593, 1984. Cited in the applicaitonon p. 13, lines 15–20.

Sackner, M. A., Rao, A. S. V., Birch, S., Atkins, M., Gibbs, L. and Davis, B.: Assessment of time-volume and flow–volume components of forced vital capacity measurement with spirometry, body plethysmography and respiratory inductive plethysmography in non-smokers and smokers. Chest 82: 272–276, 1982. Cited in the application.on p. 14, lines 5–10.

Gelb, A. F., Tashkin, D. P., Epstein, J. D., Szeftel, A. And Fairshter, F.: Physiologic characteristics of malignant unilateral main-stem bronchial obstruction. Am. Rev. Respir. Dis. 138: 1382–1385, 1988. Cited in the application on p. 14, lines 18–21.

Primary Examiner—Kyle L. Howell
Assistant Examiner—K. M. Pfaffle
Attorney, Agent, or Firm—Cohen, Pontani, Lieberman & Pavane

[57] ABSTRACT

A non-invasive method and apparatus for monitoring individual lung function is disclosed. A transducer (12, 14) is disposed on the torso above the lung to be monitored, the transducer producing a signal corresponding to movement of the torso portion therebeneath which, in turn, corresponds to changes in the volume of the underlying lung. Regional lung volume changes may also be assessed by utilizing transducers positioned on the torso to encompass only a portion of the underlying lung.

39 Claims, 11 Drawing Sheets

EFFECT OF BREATHING PATTERNS ON INDIVIDUAL LUNG VENTILATION

| BREATHING PATTERN | SEMI-RECUMBENT | SUPINE | RLD | LLD |
|---|---|---|---|---|
| NATURAL BREATHING | 48.2 (4.7) | 47.6 (6.0) | 46.8 (5.0) | 56.7 (6.8) |
| RIB CAGE (ABNORMAL PARADOX) | 51.6 (5.2) | 51.6 (2.0) | 50.4 (9.8) | 52.5 (6.5) |
| ABDOMINAL (RIB CAGE PARADOX) | 46.4 (4.4) | 46.9 (2.2) | 67.5 (8.1)* | 70.1 (10.0)* |

NON-INVASIVE ESTIMATION OF INDIVIDUAL LUNG FUNCTION

BACKGROUND OF INVENTION

One method for assessing individual lung function in humans is bronchospirometry. Bronchospirometry consists of introducing a two lumen catheter into the trachea under topical anesthesia and placing its tip at the carina such that its two distal orifices are directed to the right and left main bronchi. Elastic cuffs around the distal portion of the catheter are inflated with air to achieve a tight seal of the outer surface of the tubes to the inner walls of the bronchi. Individual lung function is then monitored by connecting the proximal ends of the catheters to separate volume or flow monitoring devices, such as spirometers or I. Review of the Literature. J. Lab & Clin. Med. 39 917-934, 1952.

A second approach for assessing individual lung function is nuclear scanning of the lungs after inhalation of a radioactive, insoluble tracer gas. Scanning of the lungs with collimators or a gamma camera after inhalation of a radioactive, insoluble tracer gas, such as Xenon$^{133}$, was first introduced in the 1960's and has largely supplanted bronchospirometry. Ball, W.C. Jr., Stewart, P.B., Newsham, I.G.S., and Bates, D.V.: Regional Pulmonary Function Studied with Xenon$^{133}$. J. Clin. Invest. 4: 519-531, 1962. Scanning avoids the invasiveness of bronchospirometry and also provides information on regional ventilation within each lung. However, scanning of the lungs for concentration of radioactive gas cannot directly estimate the absolute values of static lung volumes nor ventilation, as does bronchospirometry. Instead, pulmonary scanning is first carried out after equilibration of the radioactive insoluble tracer gas has been achieved by causing the subject to rebreathe into a closed system. Scanning is then continued as the subject breathes to the room environment and gas is washed out from the lungs. This procedure enables computation of whole lung or regional ventilation/volume ratios.

Another prior art technique, fluorodensitometry, is useful for assessing individual lung function, regional ventilation within each lung, static lung volumes, evaluations based on forced respiratory maneuvers, and phase shifts. While useful for all these purposes, a major drawback of fluorodensitometry is that it requires impacting the subject with x-rays, and consequently is totally unsuited for continuous monitoring, such as during operative procedures.

While, as noted, bronchospirometry can be used to assess individual lung function, bronchospirometry has several drawbacks. These drawbacks can be divided into three broad categories (1) patient, (2) operator and (3) other limitations, each of which is addressed below. Gaensler, E.A.: Bronchospirometry. I. Review of the Literature. J. Lab & Clin. Med. 39: 917-934, 1952; Gaensler, E.A. and Watson, T.R. Jr.: Bronchospirometry III. Complications, Contraindications, Technique and Interpretation. J. Lab & Clin. Med. 40: 223-251, 1952; Gaensler, E.A., Maloney, J.V., and Bjork, V.O.: Bronchospirometry. II. Experimental Observations and Theoretical Considerations of Resistance Breathing. J. Lab & Clin. Med. 39: 935-953, 1952.

Patient Factors

Patients undergoing bronchospirometry are not under basal conditions. Discomfort due to the tube, anxiety, sedation, local anesthesia, accumulation of secretions, spirometer inertia, and increased airway resistance due to the restricted lumens of the catheters all contribute to alterations of oxygen consumption, cardiac output and ventilation. Most patients hyperventilate during the procedure. Gaensler, E.A., Maloney, J.V., and Bjork, V.O.: Bronchospirometry. II. Experimental Observations and Theoretical Considerations of Resistance Breathing. J. Lab & Clin. Med. 39: 935-953, 1952.

Reactions to topical anesthesia of the airways are rare but fatal idiosyncratic reactions have occurred. Sequelae due to local trauma produced by the catheter appear after almost every procedure. These include hoarseness, dysphagia, sore throat and productive cough. Other less common effects are blood streaked sputum and major hemoptysis. Chills and transient high fever are also uncommon reactions, generally subsiding within a few hours, and are attributed to transient bacteremia common in other endoscopic procedures. Finally, intubation with the bronchospirometry catheter in patients with bronchial asthma may precipitate an asthmatic episode.

Absolute contraindications to bronchospirometry include tuberculous ulceration of the trachea, larynx or left main bronchus, and within two weeks of hemoptysis. Relative contraindications include deformed tracheobronchial tree, obstruction of the left main bronchus, high fever, presence of highly viscid sputum, and severe bronchiectasis. Gaensler, E.A., Maloney, J.V., and Bjork, V.O.: Bronchospirometry. II. Experimental Observations and Theoretical Considerations of Resistance Breathing. J. Lab & Clin. Med. 39: 935-953, 1952.

All bronchospirometric catheters restrict the airway lumen to an extent dependent upon the catheter design. As such, the resistance to airflow can be considerable, giving rise to the sensation of breathlessness. Theoretically, patients with limited respiratory reserve might develop respiratory insufficiency because of the added resistive load of the bronchospirometric catheters.

Operator Skills

The peroral intubation and passage through the larynx of the large bronchospirometry catheter requires considerable operator skill. This procedure is generally accomplished by highly trained thoracic surgeons, pulmonologists, anesthesiologists, and otolaryngologists. It is a skill which has generally been lost because of the widespread substitution of nuclear scanning techniques.

Other Limitations

The resistance to airflow at rates from 5 to 40 liters/min for various bronchospirometric catheters is 4 to 18 times greater than the resistances encountered in the normal respiratory passages and are equal to, or at worst four times greater than, pressure gradients encountered in airways of severe asthmatics and emphysematous patients. Unequal resistances of the two main bronchi during bronchospirometry favor distribution of ventilation to the right lung. Gaensler, E.A., Maloney, J.V., and Bjork, V.O.: Bronchospirometry. II. Experimental Observations and Theoretical Considerations of Resistance Breathing. J. Lab & Clin. Med. 39: 935-953, 1952. Thus, the average ventilation to the right lung in normal subjects has been generally found to range from 54 to 55% of the total. It has been speculated that the lesser ventilation of the left lung is an artifact due to the greater length of the catheter on the left side. Gaensler, E.A.: Bronchospirometry. I. Review of the Literature. J. Lab & Clin. Med. 39: 917-934, 1952. In addition, stenosis of the end of the catheter lying in the left main bronchus may occur more easily that on the right because of accumulated secretions. Finally, the high resistance of the catheter may cause gas trapping with elevation of end-expiratory lung volume. Gaensler, E.A., Maloney, J.V., and Bjork, V.O.: Bronchospirometry. II. Experimental Observations and Theoretical Considerations of Resistance Breathing. J. Lab & Clin. Med. 39: 935-953, 1952.

The resistance of the bronchospirometric catheter hampers investigation of the dynamic properties of the individual lungs. Thus, forced inspiratory and expiratory maneuvers, which are standard tests of overall lung function in the pulmonary function laboratory, cannot be utilized during bronchospirometry. These include forced expiratory volume delivered in one second ($FEV_{1.0}$), timed vital capacity and flow-volume curves. The high resistance of the bronchospirometric catheters also limits the utilization of the bronchospirometer to resting procedures. Finally, phase shifts with change of respiratory frequency due to internal ventilation between diseased lungs as a result of different time constants cannot accurately be measured with bronchospirometry owing to the masking of this effect by the high resistance tubing. Nor can bronchospirometry detect pendelluft, as the lungs are isolated from each other during bronchospirometry, and consequently there is no path for gas flow between the lungs.

SUMMARY OF THE INVENTION

The purpose of the present invention is a non-invasive substitute for direct measurements of individual lung function which, as noted, is currently achievable only through bronchospirometry. The major indication for assessing individual lung function involves preoperative assessment prior to contemplated lung resection. For example, if a lung to be removed because of malignant neoplasm contributes only a small fraction of the total ventilation and volume, then prognosis is much better than if the lung to be resected contributes a large fraction of the total ventilation and volume. Assessment of individual lung function can also be utilized to assess the severity of unilateral pleural disease and airway stenosis since this appears to be more disturbing to individual lung function than diffuse parenchymal disease. Assessment of individual lung function is also indicated in patients who have unexplained dyspnea and may be used to assess postoperative status in patients who have undergone partial unilateral lung resections. Gaensler, E.A., Patten, W.E. and Frank, N.R.: Bronchospirometry. VII. Indications. J. Lab & Clin. Med. 41: 456-477, 1953; Gaensler, E.A. and Watson, T.R. Jr.: Bronchospirometry III. Complications, Contraindications, Technique and Interpretation. J. Lab & Clin. Med. 40: 223-251, 1952.

Broadly speaking, the invention comprises a non-invasive method for monitoring individual lung function in a subject comprising disposing a transducer on a portion of the subject's torso above the lung to be monitored, said transducer producing a signal corresponding to movement of the torso portion therebeneath; and monitoring the signal generated by said transducer, said signal corresponding to volume changes in the underlying lung. An apparatus for effecting the method is also disclosed.

The present invention is based upon our discovery that respiratory inductive plathysmographic transducer bands of the type disclosed in U.S. Pat. No. 4,308,872, the entire contents of which are hereby incorporated by reference herein, can be placed on each hemithorax to monitor ventilation from each lung. In a typical application in adults, a 2.5 cm wide RIP transducer band is placed over each shoulder, each band forming a continuous loop that courses, anteriorly, vertically just inside the mid-clavicular line, then passes horizontally at the lower rib cage 2 to 4 cm below the nipple line, and finally courses, posteriorly, back to the shoulder near the mid-scapular line. Each such band, designated herein as a hemithoracic inductive plethysmographic (HETIP) transducer band, can be taped to the skin or held in place by a horizontal belt at the lower rib cage. Alternatively, each HETIP band may comprise a horizontally oriented oval shape having one end terminating on the front of the subject near the mid-clavicular line and the other end terminating on the back of the subject near the mid-scapular line.

With the bands so placed, lung volume changes accompanying respiration result in changes in the configuration of the areas underlying the bands. In a manner more fully explained in U.S. Pat. No. 4,308,872, changes in inductance induced in the bands by virtue of these changes may be converted to proportional voltage changes suitable for display as real time analog waveforms. In accordance with the invention, we have discovered that the waveforms from the individual bands are indicative of changes in the volume of the respective underlying lung. Consequently, the present invention is capable of measuring static lung volumes and related lung function indicators heretofore only obtainable with bronchospirometry, but without the invasiveness of that technique. In addition to the band placements indicated above, additional smaller HETIP bands may be placed over the upper thorax for accommodating regional measurements.

We have observed that the volume-motion coefficients of an HETIP transducer band placed on one hemithorax may differ from the one placed on the other hemithorax as a result of differences in electrical properties between the bands and circuits as well as the mechanical properties of the chest wall. Therefore, it is necessary to calibrate the electrical gains of each HETIP transducer to obtain valid volume estimations for each lung, and it is expected that recalibration may be necessary with changes in body posture.

To this end, we have discovered that the QDC calibration technique disclosed in commonly owned U.S. Pat. No. 4,834,109, the entire contents of which are incorporated herein by reference, is effective for calibrating the HETIP bands used in the present invention. The QDC procedure described in said patent, which is therein disclosed for calibrating respiratory inductive plethysmographic bands disposed about the rib cage and abdomen for measuring tidal volume and related parameters, finds application here because the right and left hemithoraces potentially can move with two degrees of freedom of motion. While this does not occur in normal humans, if the phrenic nerves supplying the right and left portions of the diaphragmatic muscle are stimulated 180° out of phase, as can be accomplished in anesthetized dogs, then the descent of the right diaphragm and relaxation of the left causes air from the left lung to flow into the right and conversely. This situation produces total internal ventilation without displacement of air in and out of the trachea. Wanner, A., and Sackner, M.A.: Transvenous Phrenic Nerve Stimulation in Anesthetized Dogs. J. Appl. Physiol. 34: 489-494, 1973.

This situation is analogous to the isovolume maneuver described in said patent in which volume is voluntarily shifted between the rib cage and abdominal compartments without air displacement in and out of the trachea. The isovolume maneuver demonstrates that the total respiratory system can be treated as having two degrees of freedom of motion, viz. the rib cage and abdominal compartments, and is the basis for the QDC procedure for calibrating tidal volume as measured by RIP transducer bands placed over the rib cage and abdomen as described in U.S. Pat. No. 4,834,109. In an analogous way, the calibration method for setting the electrical gains of the HETIP transducers hinges on small variations in the proportion of right to left lung volume excursions with each breath. Using statistical means to approximate a near constant volume, the calibration factor or proportionality constant for the electrical gains between the right and left HETIP transducer bands can be expressed as:

$$K = SD\ VL_{LL}/SD\ uV_{RL}$$

Where K is the proportionality constant, SD $VL_{LL}$ the standard deviation of breath by breath uncalibrated left lung volume excursions, and SD $uV_{RL}$ the standard deviation of the uncalibrated right lung volume excursions.

In six normal men, the calibration factor K determined with the QDC procedure varied as a function of body posture. Means and standard deviation (in parentheses) (SD) of K values for various body postures were (a) semi-recumbent 0.92 (0.11), (b) supine 1.03(0.18), (c) right lateral decubitus 0.76(0.20) and (d) left lateral decubitus 1.30(0.41). Mean right and left lateral decubitus values were significantly different ($p<0.05$). The percent right lung ventilation in semi-recumbent posture was 48.2(4.7)% and in supine posture 47.6(6.0)%. This is close to the equal distribution of ventilation between the two lungs expected during natural breathing since the resistive load imposed by the bronchospirometric catheter is not present. Such values held over a wide range of K values computed with the QDC procedure thereby supporting the validation of this calibration procedure.

As confirmation of the method and apparatus of this invention, in the six normal men in the preceding investigation, no phase shifts between right and lung ventilation were observed even at respiratory rates up to 100 breaths/minute. This was demonstrated by measuring the TCD/$V_T$ ratio of the separate lungs in a manner similar to that described for rib cage and abdominal compartments as described in commonly owned U.S. Pat. No. 4,777,962. Also, in agreement with bronchospirometric observations (Gaensler, E.A.: Bronchospirometry. I. Review of the Literature. J. Lab & Clin. Med. 39: 917-934, 1952), compression of one hemothorax by sandbags did not alter fractional ventilation between the right and left lungs as determined with the HETIP bands. Similarly, in agreement with bronchospirometric observations (Rothstein, E., Strzelczyk, R.: Voluntary Unilateral Breathing. Am. Int. Med. 34: 401-406, 1951), voluntary unilateral breathing did not alter fractional ventilation between the right and left lungs as determined with the HETIP bands. In this regard, fluoroscopic observations in the bronchospirometry experiments indicated that unilateral chest wall movements were present, but disclosed no difference in right and left diaphragmatic excursions, thereby accounting for the lack of change in fractional distributional ventilation of the two lungs. Rothstein, E., Strzelczyk, R.: Voluntary Unilateral Breathing. Am. Int. Med. 34: 401-406, 1951.

Since this new method of hemithoracic inductive plethysmography does not superimpose a resistive load on the respiratory system as does the relatively narrow bronchospirometric catheter, measurements of dynamic volume and flow events can be readily obtained. For example, $FEV_{1.0}$, flow-volume loops and partial flow-volumes loops, timed vital capacity and the phase angle between right and left lung volume excursions as a function of frequency, etc. can be measured. Sackner, M.A., Gonzalez, H. Rodriguez, M., Belsito, A., Sackner, D.R. and Grenvik, S.: Assessment of Asynchronous and Paradoxic Motion Between Rib Cage and Abdomen in Normal Subjects and in Patients with Chronic Obstructive Pulmonary Disease. Am. Rev. Respir. Dis. 130: 588-593, 1984). Further, individual lung function can be monitored in any posture at rest and upon exertion. Finally, the fractional contribution of right and left lung volume excursions to static lung volumes such as vital capacity, inspiratory capacity, and expiratory reserve volume can also be computed.

During forced expiration maneuvers, airway obstruction produces an added volume on the respiratory inductive plethysmograph waveform due to gas compression, which is not present on the volume signal at the airway measured with spirometry. Sackner, M.A., Rao, A.S.V., Birch, S., Atkins, M., Gibbs, L. and Davis, B.: Assessment of Time-Volume and Flow-Volume Components of Forced Vital Capacity Measurement with Spirometry, Body Plethysmography and Respiratory Inductive Plethysmography in Non-Smokers and Smokers. Chest 82: 272-276, 1982. This phenomenon of gas compression can be isolated to the individual lung with the hemithoracic inductive plethysmograph in the case of major bronchial obstruction with neoplasm or a foreign body, since the method and apparatus for the invention measures changes in thoracic gas volume. As is true of waveforms for the respiratory inductive plethysmograph and spirometer, here too, gas compression is particularly marked on the flow-volume loops obtained with the present invention, but not on flow-volume loops obtained with spirometry. Gelb, A.F., Tashkin, D.P., Epstein, J.D., Szeftel, A. and Fairshter, F.: Physiologic Characteristics of Malignant Unilateral Main-Stem Bronchial Obstruction. Am. Rev. Respir. Dis. 138: 1382-1385, 1988.

The hemithoracic inductive plethysmograph can be utilized alone or in conjunction with commercially available Respitrace ™ systems of the type described in U.S. Pat. No. 4,308,872, which monitor volume excursions of the entire rib cage and abdomen. Alternately, the hemithoracic inductive plethysmograph can be first calibrated with the QDC procedure, the calibrated signal summed and then utilized as the uncalibrated rib cage component for a Respitrace system. In that event, the QDC or other calibration methods can then be utilized to calibrate the uncalibrated summed signal of the hemithoracic inductive plethysmograph with the usual abdominal signal from the respitrace system to enable simultaneous monitoring of individual lungs, the rib cage compartment, and the abdominal compartment.

In addition to the preoperative assessment of separate lung function, the continuous nature of the hemithoracic inductive plethysmograph recording accommodates monitoring of individual lung function of intubated patients undergoing surgery or mechanically ventilated in critical care units to detect slippage of the endotracheal tube into a main bronchus with subsequent underventilation of the contra lateral side. Further, unilateral mucus plugging of the airways with subsequent underventilation of the affected lung can be detected early with the hemithoracic inductive plethysmograph to alert health care personnel to the prompt need for suctioning the airways in patients with retained airway secretions. Unilateral underventilation as determined with the present invention also allows early detection of pneumothorax, pleural effusion, unilateral diaphragmatic paralysis, hemipareses after cerebrovascular accident, and atelectasis in critically ill patients. It has been found that the latter usually are better detected as respiratory rate increases (either voluntarily, during exercise or during controlled mechanical ventilation), as both underventilation and phase shifts between the two HETIP bands increases with increasing respiratory frequency.

Further features and advantages of the method and apparatus in accordance with the present invention will be more fully apparent from the following detailed description and annexed drawings of the presently preferred embodiments thereof.

DETAILED DESCRIPTION OF THE PREFERRED EMBODIMENTS

Figure 1A:
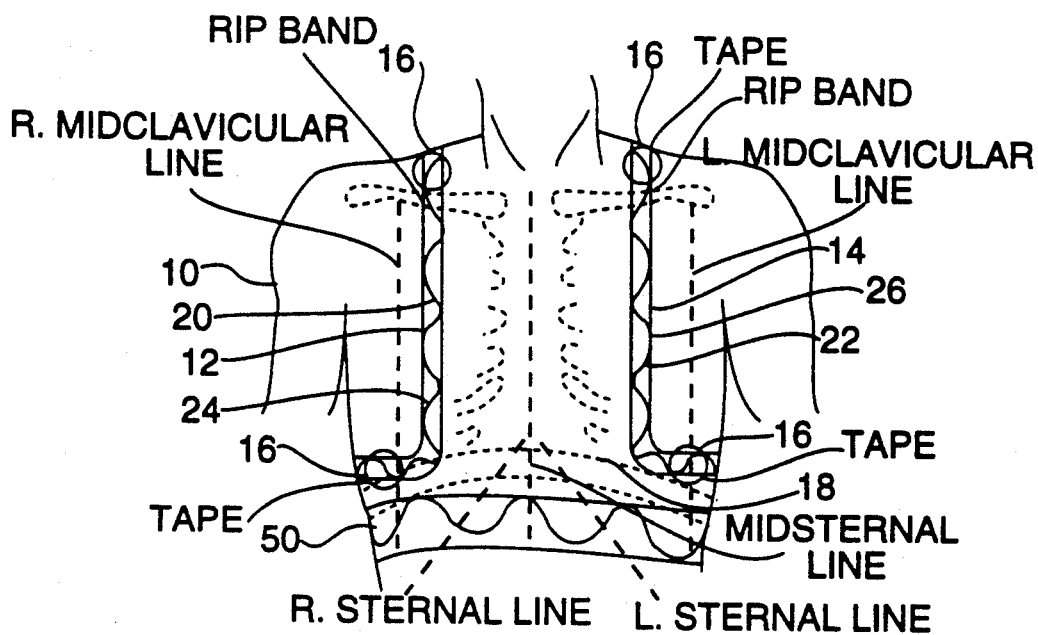
FIGS. 1A-1C illustrate securement of hemithoracic inductive plethysmographic transducer bands to a subject's torso for measuring individual lung function.
Figure 1B:
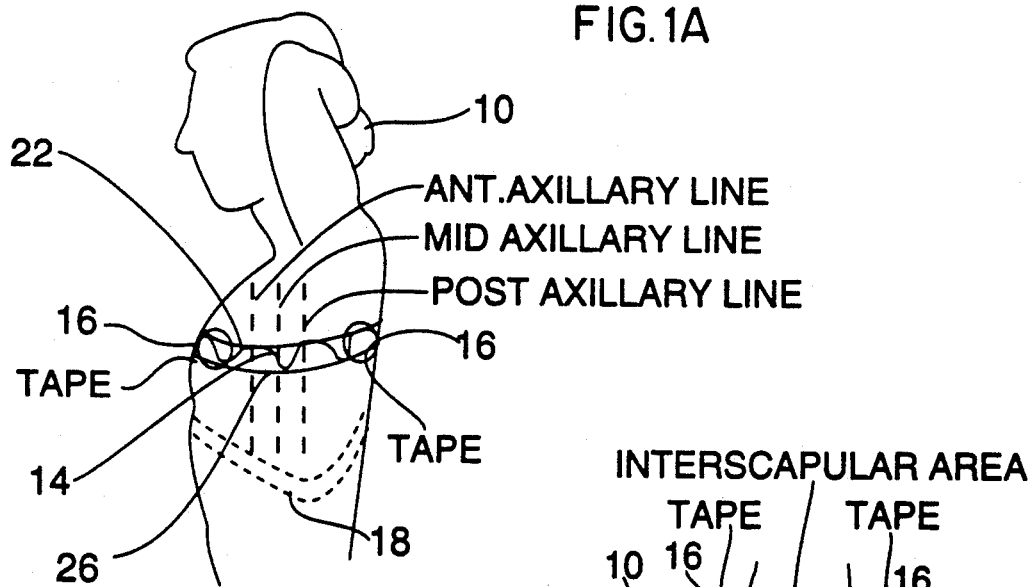
Figure 1C:
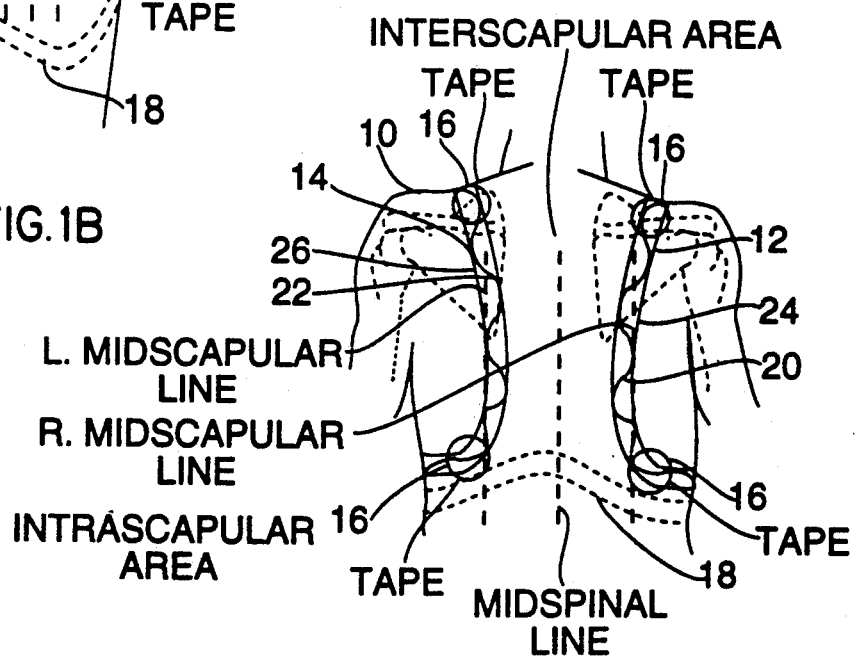

Referring now the drawings, and initially to FIG. 1 thereof, placement of hemithoracic inductive plethysmographic transducer (HETIP) bands 12, 14 for monitoring right and left lung function, respectively, is illustrated. As noted above, each transducer band may comprise a transducer of the type disclosed in commonly owned U.S. Pat. No. 4,308,872, which is herein incorporated by reference, though, as will be more fully apparent as this description progresses, other transducers may be substituted.

As illustrated, for an average adult each transducer band 12, 14 is a continuous loop about 2.5 cm wide that courses, anteriorly, vertically just inside a right and a left mid-clavicular line respectively, then passes horizontally at the lower rib cage about 2-4 centimeters below the nipple line, and finally courses, posteriorly, vertically back to the left and right, respectively shoulder near the left and right mid-scapular lines, respectively. The transducer bands 12, 14 can be held in place by tape patches 16 or, alternatively, by a belt or band extending about the lower rib cage and represented by the dotted lines 18 in FIG. 1. Whatever method of securement is selected, care should be taken not to inhibit movement of the vertical portions on the chest and back, as movement of those portions in response to breathing is necessary for accurate lung function measurements in accordance with the invention.

As more fully explained in U.S. Pat. No. 4,308,872, each band 12, 14 incorporates a conductive loop 20, 22, e.g. a wire, secured in any suitable fashion to elastic bands 24, 26, respectively, such that the wires 20, 22 expand and contract with expansions and contractions of the rib cage. Consequently, as the subject 10 breathes, the elastic bands 24, 26 and hence the wires 20, 22 secured thereto expand and contract, resulting in changes in the inductance of the wires. Using known techniques, such as those described in U.S. Pat. No. 4,308,872, the inductance of each loop may be converted to a proportional voltage signal. For example, as described in U.S. Pat. No. 4,308,872, each wire 20, 22 may be incorporated as the inductance element of an LC oscillator, such that the frequency of the oscillator varies proportionally to changes in the inductance of the wire, with these frequency changes, in turn, being converted to corresponding analog voltage signals by a frequency to voltage converter. Such an arrangement is diagrammatically illustrated in FIG. 2, wherein each wire 20, 22 serves as the inductance element of an LC oscillator, the output of which is connected to a frequency to voltage converter for generating analog voltage signals suitable for further processing.

Figure 2:
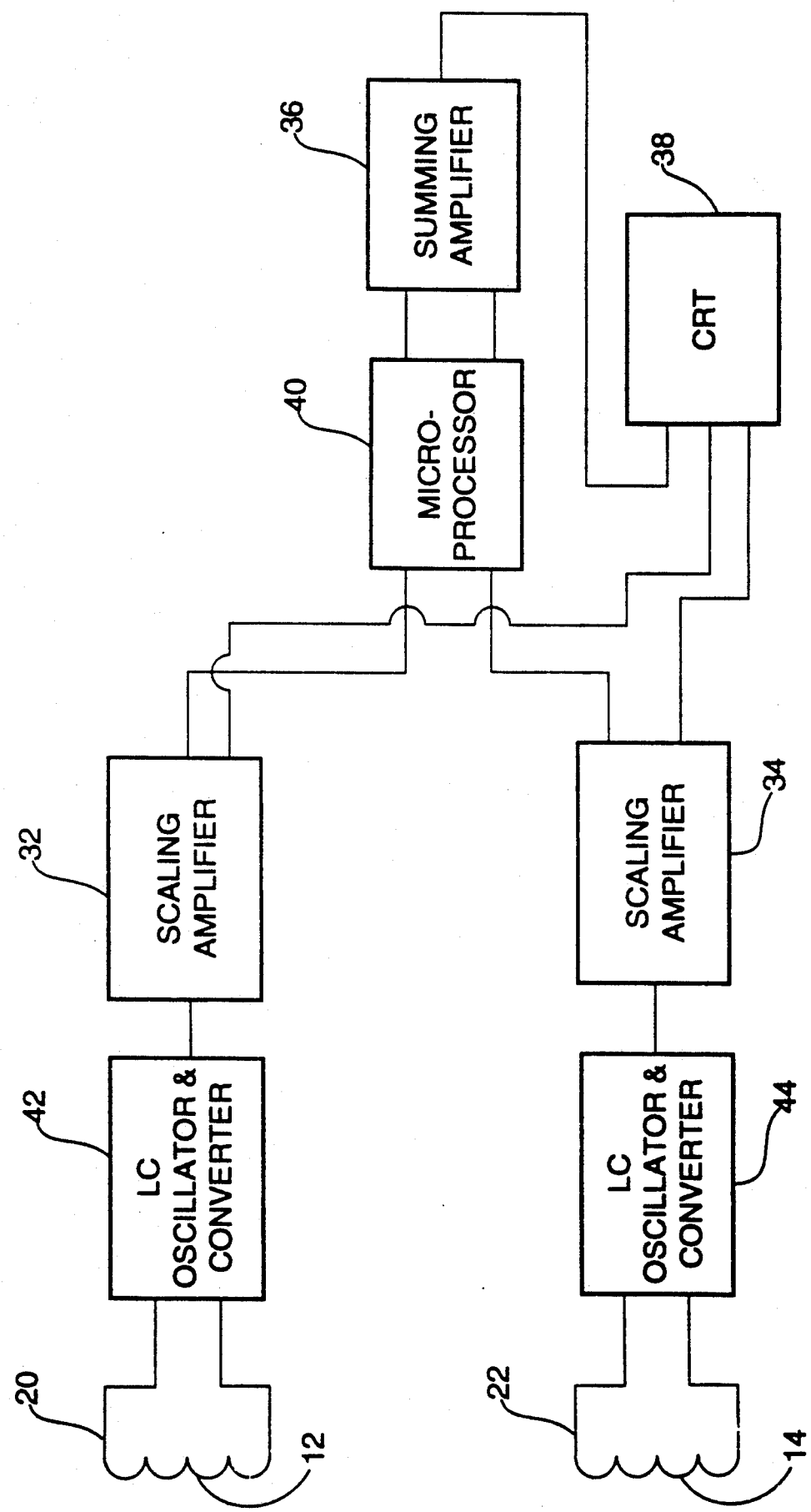
FIG. 2 is a diagrammatic representation of an apparatus for monitoring individual lung function in accordance with the invention.

In a preferred embodiment, and as shown in FIG. 2, the free ends of the wires 20, 22 are connected to modules 42, 44, each module incorporating the circuitry for the LC oscillator and frequency to voltage converter. A suitable module for this purpose is disclosed in commonly assigned U.S. Pat. No. 4,807,640 which is herein incorporated by reference and is available from Nims, Inc., Miami Beach, Fla. under the designation "oscillator set".

Referring again to FIG. 2, the output of the frequency to voltage converter in each module 42, 44 is input, via wires 46, 48, respectively, to the scaling amplifiers 32, 34. The scaling amplifiers, which have adjustable gains, are used for calibrating the signals from the right and left hemithoracic inductive plethysmographic transducer bands 12, 14, respectively, to reflect the relative contributions of the right and left lungs to total ventilation. That is, once the scaling amplifiers 32, 34 are properly adjusted, as by using the technique more fully described in U.S. Pat. No. 4,834,109 for deriving the calibration factor K, the output from each scaling amplifier 32, 34 is proportional to the relative contribution of the respective lung to total ventilation.

The calibrated signals from the scaling amplifiers 32, 34 may be summed, as by a summing amplifier 36, to yield a signal proportional to total ventilation. In lieu of a summing amplifier 36, a microprocessor 40 may be incorporated for summing the signals from the scaling amplifiers 32, 34 and/or further processing those signals for diagnostic purposes, all in accordance with techniques known to those of ordinary skill in the art. The output signal from the summing amplifier 36 or microprocessor 40 as well as the output signals from the scaling amplifiers 32, 34 may be displayed as on a graphic recorder, digital volt meter, or a CRT, all of which are diagrammatically represented by the block 38 in FIG. 2.

Preferably, the wires 46, 48 from the modules 42, 44 are input to an apparatus available from Nims, Inc. and marketed under the designation Respigraph TM. The Respigraph TM incorporates scaling amplifiers 32, 34, a summing amplifier, and circuitry for executing the preferred calibration technique described in commonly assigned U.S. Pat. No. 4,834,109.

Figure 3:
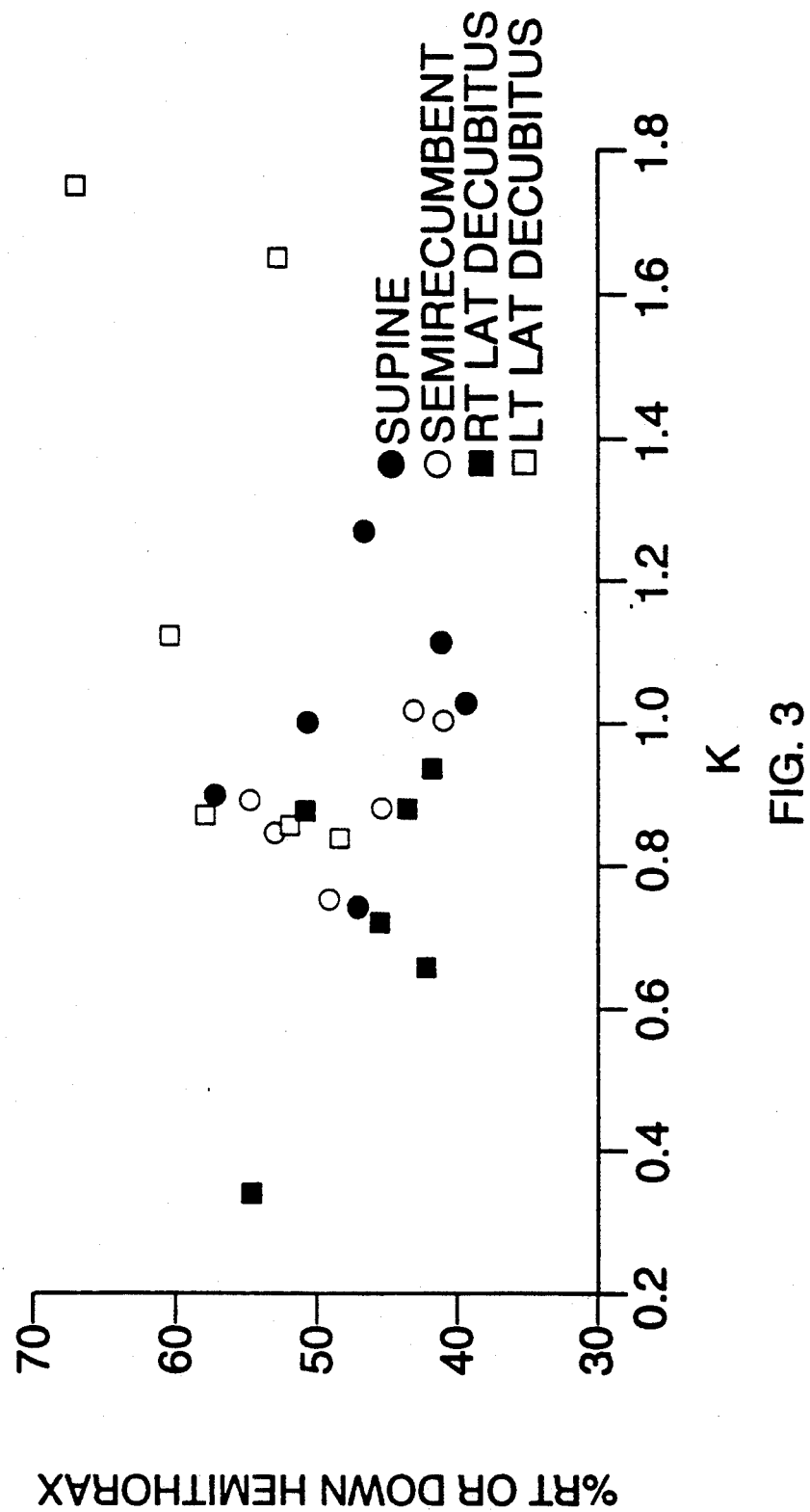
FIG. 3 is a graph illustrating the validity of the calibration technique proposed for use with the present invention.

Referring now to FIG. 3, to validate the calibration procedure described in commonly owned U.S. Pat. No. 4,834,109 for use with the present invention, we utilized that procedure to calculate the calibration factor K for a normal subject in a variety of positions, namely, supine, semi-recumbent, right lateral decubitus and left lateral decubitus. In FIG. 3, the ordinate represents the percent contribution of one lung to total ventilation for the normal subject studied. For the supine, semi-recumbent and right lateral decubitus positions, the ordinate represents the percent contribution of the right lung to total ventilation, whereas for the left lateral decubitus position, the ordinate represents the percent contribution of the left lung. For a normal subject, it would be expected that the percent contribution for each lung would be about fifty percent, and indeed the graph of FIG. 3 bears that out, thereby suggesting that the calibration technique is valid. It should be noted that recalibration was carried out for each change in body posture, and it appears that this is a prerequisite to valid results.

Figure 4:
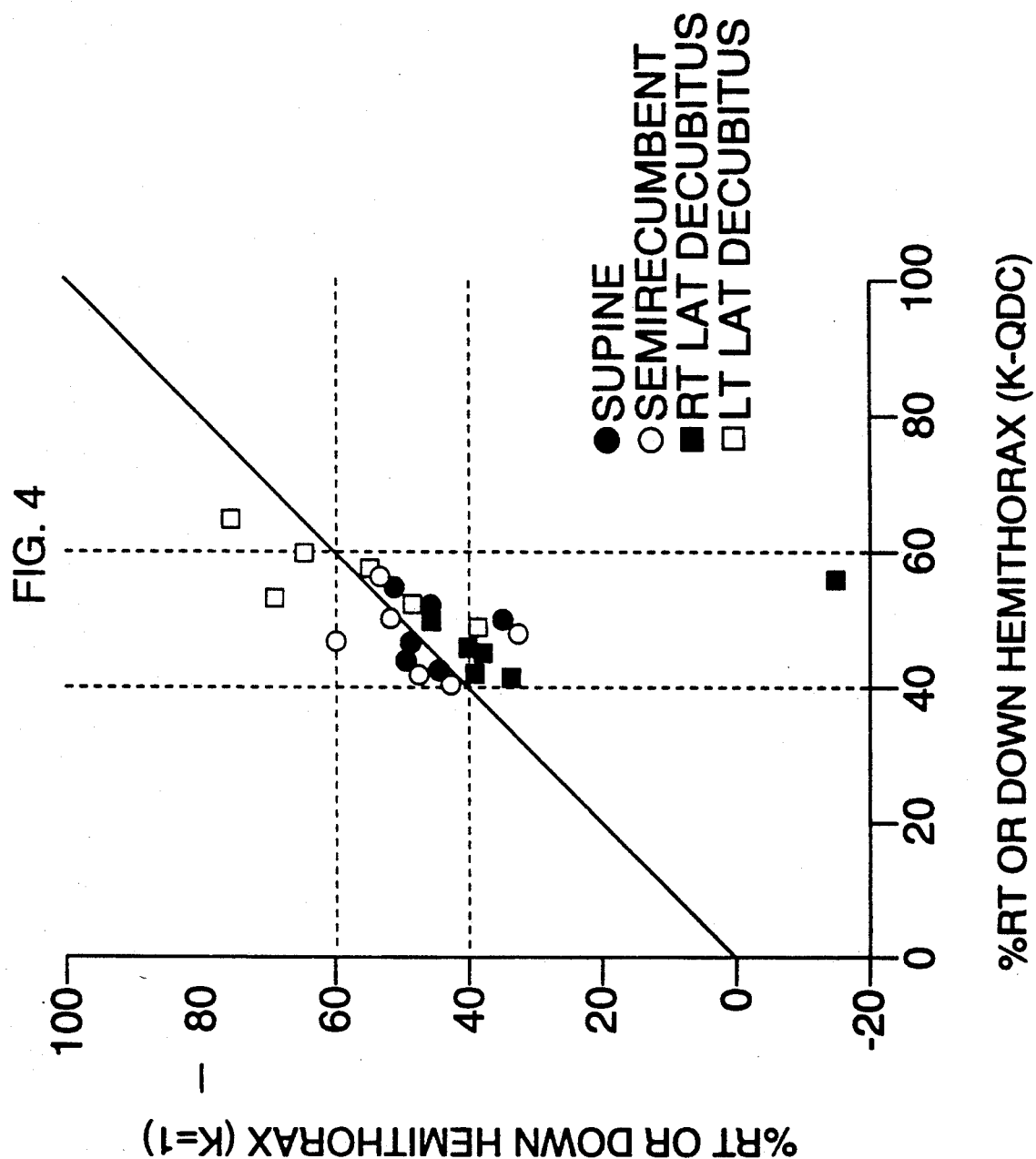
FIG. 4 is another graph illustrating the validity of the calibration technique.

To further validate the calibration technique of said U.S. Pat. No. 4,834,109 for use in the present invention, we compared the percent contribution of one lung to total ventilation based on the assumption of a K factor of 1 with the percent contribution of that lung to total ventilation using a K factor calculated in accordance with the technique of said U.S. Pat. No. 4,834,109. This data, for a normal subject, is depicted in FIG. 4, with recordings once again being taken with the subject in the supine, semi-recumbent, right lateral decubitus and left lateral decubitus positions. In FIG. 4, the ordinate represents the percent contribution of one lung (the right lung except for the left lateral decubitus position) to total ventilation based on the assumption of a K factor of 1, and the abscissa represents the percent contribution of one lung (again the right lung except for the left lateral decubitus position) to total ventilation based on a calculated K factor. As shown, when a K factor of 1 was assumed, many of the recorded values fell outside of the expected 40 to 60 percent range (i.e. 40 to 60 percent contribution of one lung to total ventilation), whereas when the K factor was calculated in the manner suggested herein, the great majority of the values fell within the expected 40 to 60 percent range. This is further evidence of the validity of the calibration technique of said U.S. Pat. No. 4,834,109 for use with the present invention. The solid line in FIG. 4 simply indicates points at which the percent contribution of the measured lung would be the same both with an assumption of a K factor of 1 and with a calculated K factor. As shown, only a few points fall on the solid line.

Figures 5, 6:
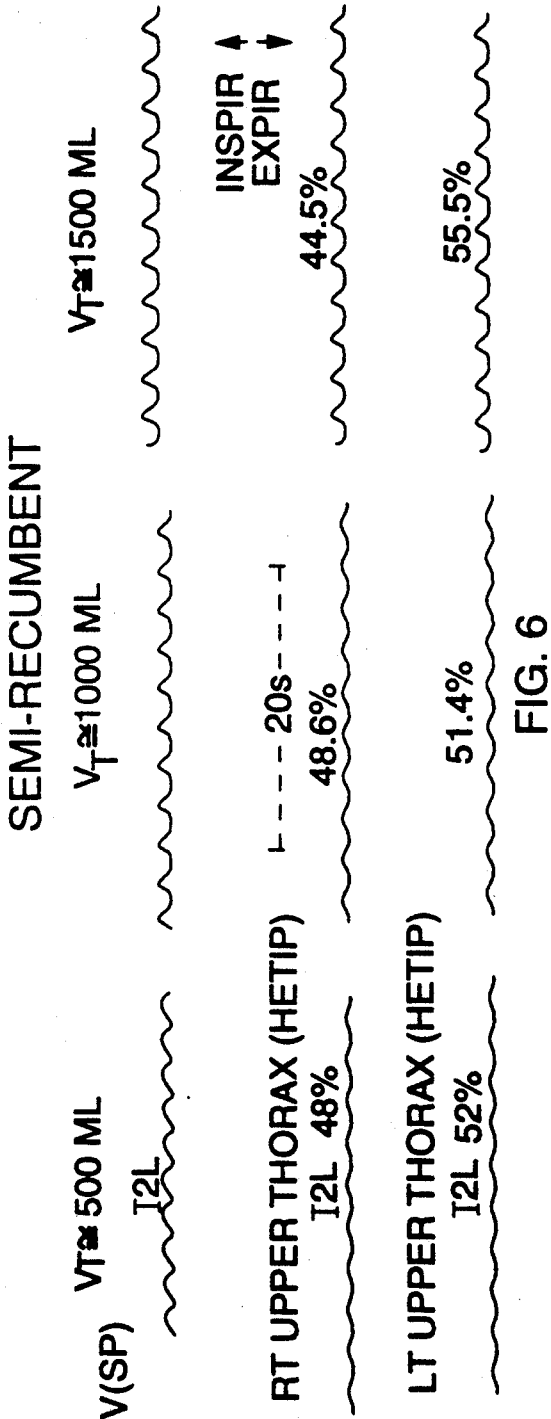
FIG. 5 is a chart further evidencing the validity of the calibration technique.
FIG. 6 shows recordings obtained with the present invention with increasing tidal volumes.

To further validate the use of the calibration technique, after calculating the K factor for a normal subject, we instructed the subject to breath normally, with paradoxical abdominal movement, and with paradoxical rib cage movement. Breathing with paradoxical abdominal movement refers to breathing in which the subject intentionally moves the abdomen in a direction opposite to that accompanying normal breathing and likewise breathing with paradoxical rib cage movement is breathing in which the rib cage is intentionally moved in a direction opposite to that accompanying normal breathing. For each of the three types of breathing, we calculated the percent contribution of one lung to total ventilation with the subject in each of the by now familiar four positions, namely, supine, semi-recumbent, right lateral decubitus and left lateral decubitus. The results are shown in FIG. 5. In FIG. 5, the first number under each column heading represents the percent contribution of one lung (the right lung except in the left lateral decubitus position) to total ventilation, and the number in parentheses represents the standard deviation. As indicated by the asterisks, measurements recorded in the right lateral decubitus and left lateral decubitus positions during paradoxical rib cage breathing are outside the 40 to 60 percent range, and these values are consistent with those derived with other techniques and are due to the reduced resistance to excursions of the "down" lung in these circumstances (in the right lateral decubitus position the "down" lung is the right lung, and in the left lateral decubitus position it is the left lung).

It should be appreciated that the results shown in FIGS. 3-5 not only demonstrate the validity of the calibration technique, they also demonstrate the validity of the method and apparatus of FIGS. 1-2 for measuring the percent contribution of each lung to total ventilation, as the results are consistent with those derived empirically using other techniques, such as bronchospirometry. Of course, and as noted above, changes in total ventilation can be monitored by simply summing the calibrated signals from the right and left bands 12, 14.

Of course, all of the measurements described thus far are relative. That is, the calibrated signals from each of the bands do not indicate absolute ventilation contributions, but rather are proportional to absolute values. Absolute values can, however, be derived by first calibrating the output signals from the bands 12, 14, then measuring absolute total lung volume using an alternative technique, such as spirometry, and then proportionately adjusting the scaling amplifiers 32, 34 until the sum of the calibrated output signals from the bands 12, 14 equals the absolute value measured with spirometry. If that is done, the calibrated output signals from the left and right bands 12, 14 will indicate absolute contributions of each lung to total ventilation, and the summed signal will indicate absolute total ventilation.

FIG. 6 demonstrates the validity of the invention with different tidal volumes ($V_T$). The recordings in FIG. 6 were made after calibration with a normal subject in a semi-recumbent position The upper recording represents tidal volume as calculated with a spirometer with, from left to right, progressively deeper breathing resulting in increasing tidal volumes starting from about 500 ml and increasing to about 1500 ml. In the leftmost portion of the upper recording, the vertical line designated "2L" represents a two litre excursion, and is included for reference purposes.

The second group of recordings in FIG. 6 indicates the percent contribution of the right lung to total ventilation as determine by recordings from the band 12, with the relative contribution at each tidal volume indicated above the respective recording portion. As would be expected, the relative percent contribution remains substantially the same as tidal volume increases. The horizontal line bearing the designation "20s" above the middle recording from the band 12 represents a 20 second time span and is also included for reference purposes. As will by now be apparent, the third group of recordings is taken from the band 14 and indicates the percent contribution of the left lung to total ventilation which, as is apparent from FIG. 6, also remains substantially the same with increasing tidal volume. While the percentage contributions of each lung do not remain exactly the same with increasing tidal volumes, the changes are within statistical limits.

Figure 7:
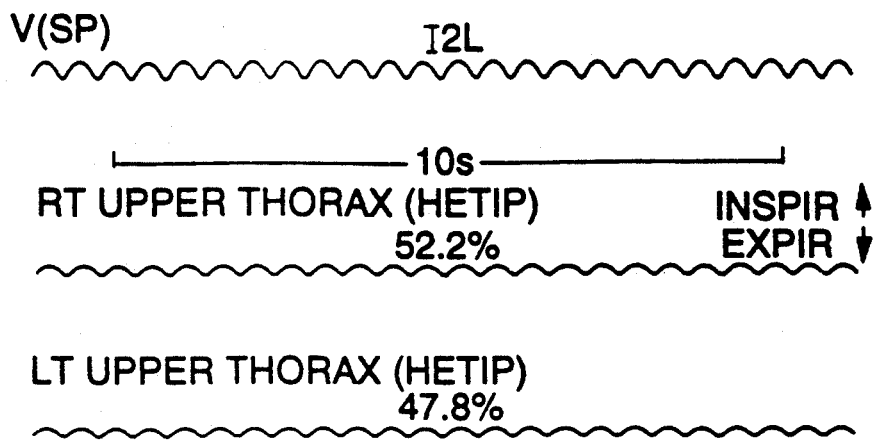
FIG. 7 shows recordings obtained with the present invention with rapid breathing.

FIG. 7, taken in conjunction with FIG. 6, establishes the validity of the present invention with increasing breathing rates. The recordings shown in FIG. 7 were taken on the same subject as in FIG. 6, but with the subject instructed to breathe at a faster rate. In FIG. 7, the horizontal line marked "10s" in the middle recording represents a 10 second interval, and a comparison of the number of breaths during that interval with the number of breaths recorded during a corresponding interval in FIG. 6 (as determined by reference to the 20 second interval designated thereon) shows that the breathing rate of the subject in FIG. 7 is substantially greater than the breathing rate in FIG. 6.

The upper, middle and bottom recordings in FIG. 7 correspond to the upper, middle and bottom recordings in FIG. 6 and represent, respectively, tidal volume, the calibrated signal from the right lung band 12, and the calibrated signal from the left lung band 14. As indicated by the percentages above the middle and bottom recordings, the percent contribution of the right and left lungs to total ventilation remains substantially at 50% at the increased breathing rate, which is expected from empirical data derived with other techniques. Accordingly, this further demonstrates the validity of the technique of the present invention.

Figure 8:
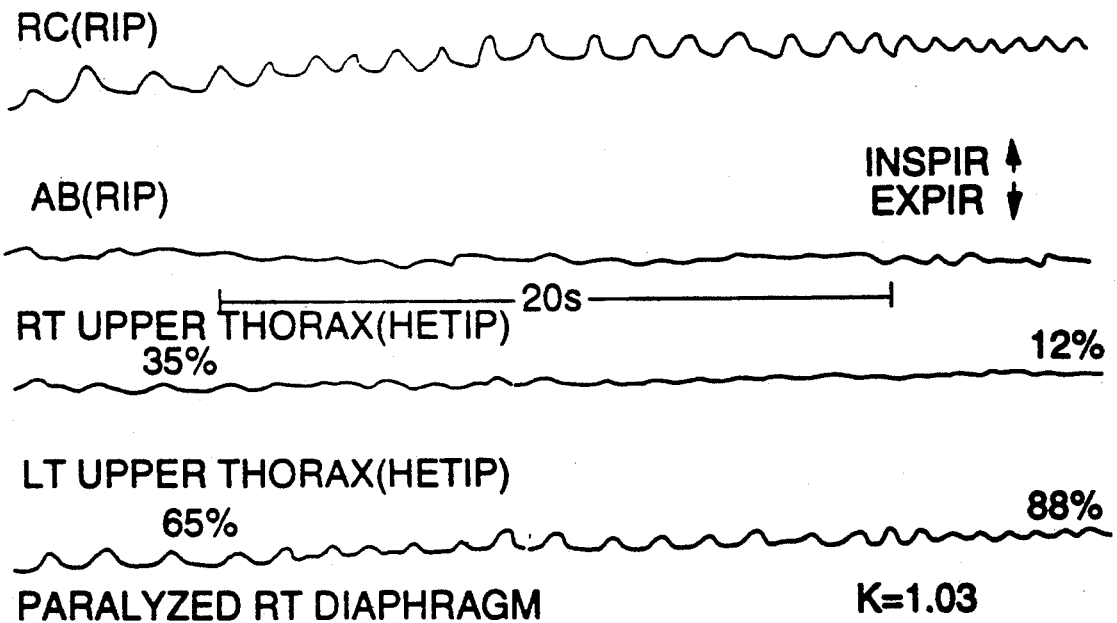
FIG. 8 shows recordings obtained with the present invention for a subject having a paralyzed right diaphragm.

FIG. 8 shows recordings from the bands 12, 14 after calibration, for a subject having a paralyzed right diaphragm and, from left to right, with a gradually increasing breathing rate. As shown by the percentages above the recordings, as the breathing rate increases, the percent contribution of the right lung to total ventilation decreases from a high of 35% to a low of 12%, while the percent contribution of the left lung increases by a corresponding amount, i.e., from a low of 65% to a high of 88%. Again, based on empirical data derived with other techniques, this would be expected for a subject with a paralyzed right diaphragm. As shown on the graph, the calibration factor for this subject, who was in the sitting position during the recordings, was 1.03.

Figure 9:
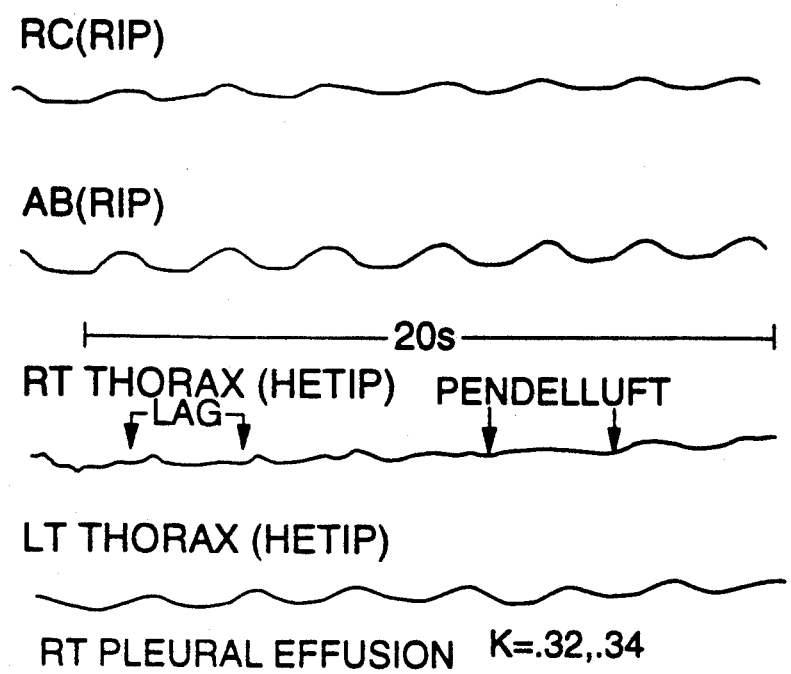
FIG. 9 shows recordings obtained with the present invention for a subject having right pleural effusion.

The recordings in FIG. 9 were taken with a subject having right pleural effusion, which is a fluid accumulation between the right lung and the chest wall. For this subject, the damping effect of the accumulated fluid results in paradoxical movement as between the right and left lungs, with the right lung shown lagging the left in FIG. 9. This lagging effect may result in pendelluft, in which air expired from one lung is inspired by the other, which could lead to a lack of oxygen and an increase in carbon dioxide, as expired air is, of course, much lower in oxygen and higher in carbon dioxide than inspired air. The two values for the calibration factor K shown at the bottom of FIG. 9 simply indicate that the K factor was calibrated twice for the subject, the two results being within statistical limits.

Figure 10:
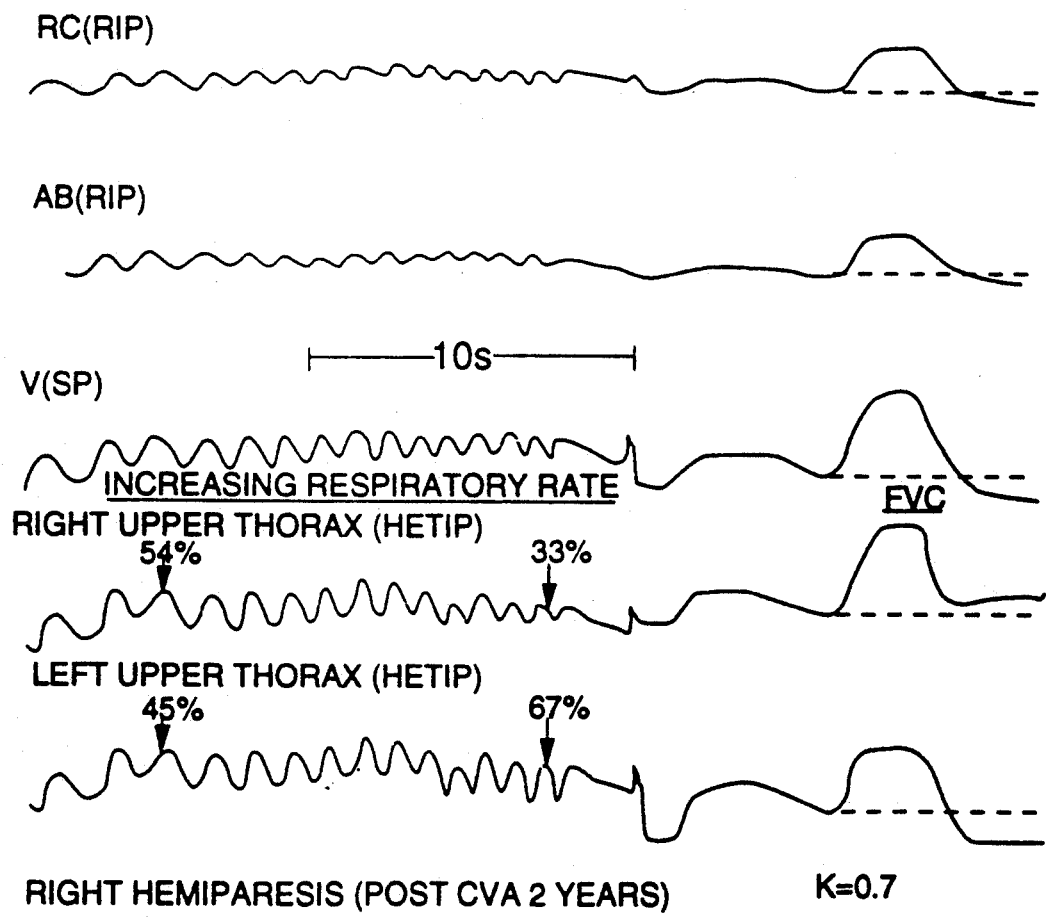
FIG. 10 shows recordings obtained with the present invention in a patient with right-sided hemiparesis following a cerebrovascular accident.

FIG. 10 illustrates findings in a patient with right-sided hemiparesis following a cerebrovascular accident. Although the HETIP tracings show normal distribution during tidal breathing, rapid breathing shows a major shift in volume to the unaffected side. Further, the end-expiratory lung volume is higher on the right side than the left side at the point where the right side receives 33% of the ventilation and the left side 67%. The failure to reach the end-expiratory lung volume level (also known as intrinsic PEEP or auto PEEP to those knowledgeable in the art) is also seen in the forced vital capacity maneuver (FVC) where the recording for the right upper thorax (HETIP) indicates that the terminal tracing does not fall below the hatched line as does the recording for the left upper thorax. In FIG. 10, the tracing V(SP) indicates total respiration volume as measured with a spirometer; RC(RIP) indicates the recording from the rib cage component of a respiratory inductive plethysmograph; and AB(RIP) indicates the recording from the abdominal component of a respiratory inductive plethysmograph.

Figure 11:
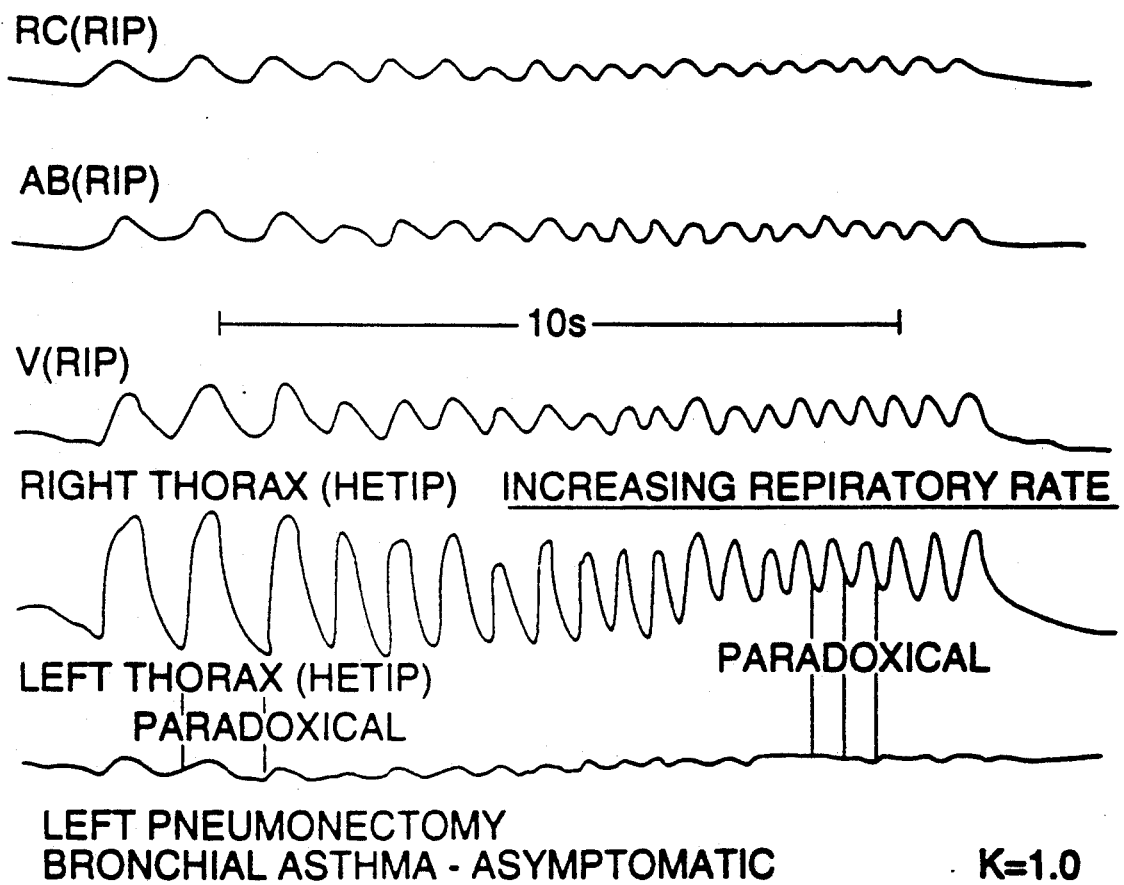
FIG. 11 shows recordings obtained with the present invention for a patient following pneumonectomy.

FIG. 11 depicts recordings in a patient following pneumonectomy. Here, the calibration technique of U.S. Pat. No. 4,834,109 was not utilized since no lung ventilation is present on the left side. Movements are still seen but result from displacements of the heart and great vessels to the pneumonecotimized side with breathing.

Figure 12A:
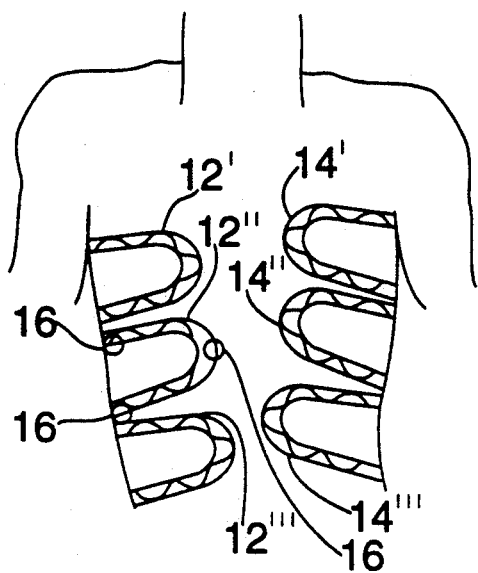
FIGS. 12A-12C are views similar to FIG. 1, but showing alternative band placements for assessing regional lung function.
Figure 12B:
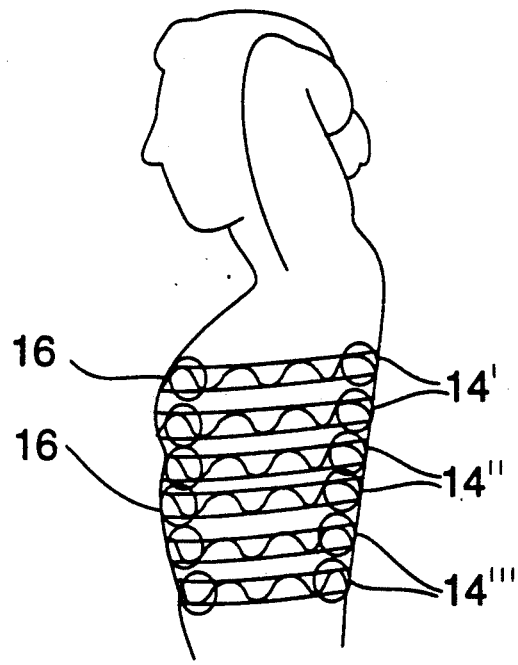
Figure 12C:
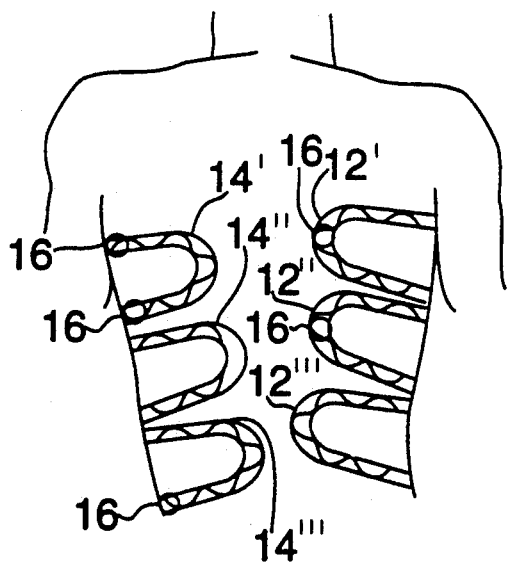

Thus far, the present invention has been shown and described for monitoring the performance of the entire left or right lung. Alternatively, or in addition, the present invention may be utilized for monitoring regional lung performance. Referring to FIG. 12, an arrangement for monitoring the performance of the upper, middle and lower regions of the right and left lungs is shown. As shown in FIG. 12, in lieu of the band placements illustrated in FIG. 1, three separate bands, each having a generally oval shape, are positioned on each lung. Looking at the right lung in FIG. 1, a first band 12' is positioned about the upper region of the right lung, a second band 12" is positioned about the middle region of the right lung, and a third band 12''' is positioned about the lower region of the right lung. As shown, each band extends from just inside the mid-clavicular line anteriorly to just inside the mid-scapular posteriorly. A corresponding arrangement of bands 14', 14" and 14''' are disposed about the upper, middle and lower regions of the left lung. As preferred and shown, the bands 12', 12", 12''', 14', 14" and 14''' are secured to the subject by a plurality of tape patches 16. Except for their size and placement, each of the bands illustrated in FIG. 12 is of similar construction to the bands 12, 14 of FIG. 1.

Each of the bands 12', 12", 12''', 14', 14" and 14''' has its own module 42', 42", 42''', 44', 44", 44''', respectively, each module incorporating the circuitry for its respective LC oscillator and frequency to voltage converter. The output of the frequency to voltage converter from each module is, in turn, input to an arrangement similar to that shown in FIG. 2, such that the signals from the bands may be calibrated and displayed. As noted above, for the embodiment of FIG. 1 the outputs from the modules 42, 44 are preferably input to a Respigraph TM, which incorporates calibration circuitry. Inasmuch as the Respigraph TM is a two channel device, the embodiment of FIG. 10 would require three Respigraphs TM, a relatively expensive proposition. Accordingly, for such an application, it is preferable to use another product marketed by Nims, Inc., Respitrak TM. The Respitrak TM is also a two channel device, and hence three Respitraks TM will be required. However, the Respitrak TM is less expensive, partly because it does not incorporate calibration circuitry. To effect calibration, the output signals from the Respitraks TM, which do incorporate scaling amplifiers, may be input to a personal computer, such as an IBM AT 386, which can be programmed to effect calibration using the technique described in U.S. Pat. No. 4,834,109. As the details of such programming are known from the prior art and within the capabilities of ordinarily skilled art workers, a further description thereof is unnecessary.

In practice, one regional band on each lung will be calibrated against its counterpart on the other lung. That is, the band 12' will be calibrated against the band 14', the band 12" against the band 14", etc. It will be apparent that once such calibration is effected, relative contributions to ventilation as between corresponding regions of the right and left lung may be determined. For example, by comparing the relative amplitudes of the calibrated signals from the upper bands 12' and 14', a comparison of the relative contributions of each may be made. This is significant, as it allows assessment of regional lung performance.

Still referring to FIG. 12, if desired the output signals from the bands 12', 12" and 12''' may be summed and calibrated against the corresponding summed signal from the bands 14', 14" and 14'''. The resulting summed, calibrated signals for each lung will then provide information corresponding to that available from the embodiment of FIG. 1. If this is done, it will be apparent that the embodiment of FIG. 12 may be used not only for assessing regional lung performance, but whole lung performance as well.

Figure 13A:
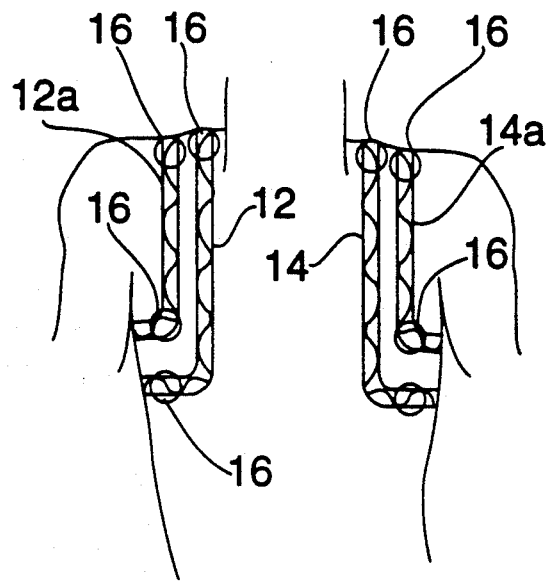
FIGS. 13A-13C are other views similar to FIG. 1, but showing alternative band placements for assessing regional and total lung function.
Figure 13B:
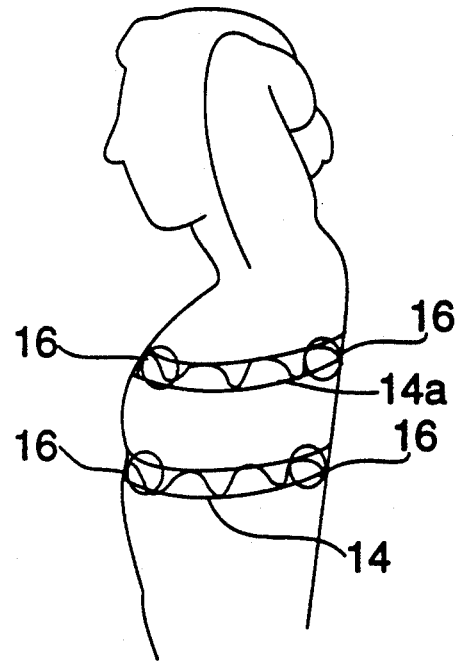
Figure 13C:
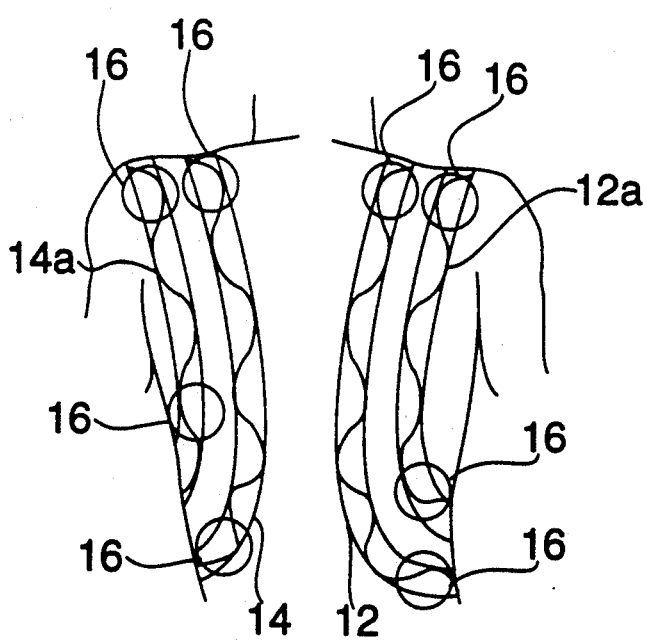

FIG. 13 shows a further alternative arrangement suitable for monitoring whole lung function and regional upper lung performance. As shown in FIG. 13, two bands are disposed about each lung. First bands, 12, 14, are configured and placed as shown in FIG. 1. Second bands 12a, 14a, having the same general configuration as the bands 12, 14, but smaller, are disposed about the upper region of the right and left lungs, respectively. As usual, the bands are preferably secured by tape patches 16.

As should now be apparent from the discussion of FIG. 12, the band 12 will be calibrated against the band 14, and the band 12a against the band 14a. Thereafter, the relative contributions of the right and left upper lung regions may be assessed by comparing the calibrated output signals from the bands 12a, 14a, respectively, while the calibrated output signals from the bands 12, 14 may be utilized in the same manner as the bands 12, 14 in FIG. 1.

Figure 14:
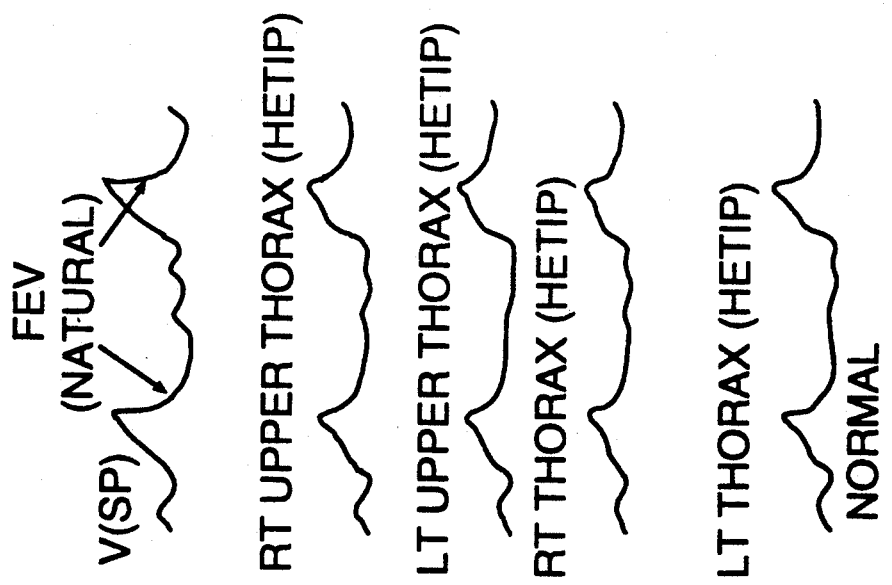
FIG. 14 shows recordings obtained with the apparatus of FIG. 11 with forced expiration.

FIG. 14 shows recordings taken from the bands 12, 14, 12a and 14a during forced expiration, i.e., where the subject, upon instruction, expires with great force. The upper tracing in FIG. 14 shows a tidal volume recording taken with a spirometer, with the vertical peaks indicating the timing of forced expirations. The second tracing shows the calibrated output signal from the band 12a in FIG. 13, the third tracing the calibrated output signal from the band 14a, the fourth tracing the calibrated output signal from the band 12 and, finally, the fifth tracing the calibrated output signal from the band 14. As shown, each of the output signals indicates an increase in contribution during a forced expiration, thereby further validating the present invention for measuring both whole and regional lung contributions to ventilation. The recordings of FIG. 14 were taken with a normal subject in a sitting position.

Figure 15:
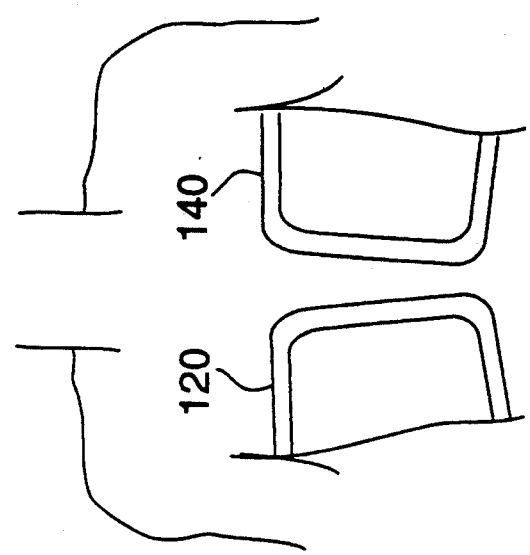
FIG. 15 is another view similar to FIG. 1, showing an alternative band placement for assessing total lung function.

As an alternative to the band placement shown in FIG. 1, bands 120, 140 having the configuration and placement shown in FIG. 15 may be utilized. Except for their placement and configuration, the output signals from the bands 120 and 140 in FIG. 15 provide substantially the same information as the output signals from the bands 12, 14 of FIG. 1.

From the foregoing, it will be apparent that the present invention is suitable for monitoring the relative contributions of each lung to ventilation, regional lung contributions to ventilation, the effects of forced and rapid respiratory maneuvers, periods of phase shift and comparative static lung volumes as measured during breathholding following a deep inhalation preceded by a forceful expiration. Moreover, the present invention effects such monitoring non-invasively, and hence is suitable for long term monitoring, and practical applications for the present invention have already been discussed above.

As a further modification, after the output signals from the right and left bands 12, 14 in FIG. 1 are calibrated and summed, the summed signal may be utilized as the rib cage signal for a respiratory inductive plethysmograph. In such event, the embodiment illustrated in FIG. 1 would further include an abdominal band 50, such that the output signal from the abdominal band and the summed signal from the bands 12, 14 may be calibrated and then summed for providing an output signal proportional to tidal volume. As the manner of calibrating and summing the rib cage and abdominal signals for respiratory inductive plethysmography for providing a signal proportional to tidal volume is well known to persons of ordinary skill in the art and described, for example, in the above-mentioned U.S. Pat. No. 4,308,872, a further description thereof is deemed unnecessary.

Finally, while particular transducers have been shown and described for use with the present invention, other transducers capable of detecting thoracic motion may be used, such transducers including the bellows pneumograph, mercury in silastic strain gauge, differential linear transformer, and inductance circumferential transducer.

While we have herein shown and described preferred embodiments of the present invention and suggested certain modifications thereto, it will be apparent to those of ordinary skill in the art who have read this description that still further changes and modifications may be made therein without departing from the spirit and scope of this invention. Accordingly, the above description should be construed as illustrative, and not in a limiting sense, the scope of the invention being defined by the following claims.

We claim:

1. A non-invasive method for monitoring individual lung function in a subject having a torso and right and left sides of the torso defined on opposite sides of a midsternal line, comprising:
   disposing a transducer on the subject's torso, said transducer being disposed on one only of the right and the left sides of the subject's torso for overlying only a portion of the chest and back of the subject's torso above an individual lung to be monitored, said transducer producing a signal corresponding to the movement of the portion therebeneath; and
   monitoring the signal produced by said transducer, said signal corresponding to volume changes in the underlying individual lung.

2. The method of claim 1, wherein said disposing step further comprises disposing at least one plethysmographic transducer.

3. The method of claim 2, further comprising the step of securing said at least one plethysmographic transducer to the subject's torso.

4. The method of claim 1, wherein said disposing step further comprises disposing a first hemithoracic transducer band on the right side of the subject for monitoring right lung functions, and wherein said method further comprises disposing a second hemithoracic transducer band on the left side of the subject for monitoring left lung functions, each of said first and second transducer bands forming a continuous loop that courses, anteriorly, vertically near a right mid-clavicular line and a left mid-clavicular line, respectively, of the subject's torso, then horizontally at a lower rib cage, and then posteriorly, near a right mid-scapular line and a left mid-scapular line, respectively, of the subject's torso vertically back to a left and right shoulder, respectively.

5. The method of claim 4, further comprising the step of securing each of said first and second plurality of transducer bands to the subject.

6. The method of claim 4, wherein each of said first and second transducer band disposing steps comprising coursing the respective transducer band horizontally at said lower rib cage about 2-4 centimeters below the subject's nipple line, and wherein each of said first and second transducer bands is about 2.5 centimeters wide.

7. The method of claim 1, wherein said disposing step comprises disposing a first plurality of inductive plethysmographic transducer bands above the left lung of the subject so that each transducer band of said first plurality of bands overlies a different portion of the left lung, said method further comprising the step of disposing a second plurality of inductive plethysmographic transducer bands above the right lung of the subject so that each transducer band of said second plurality of bands overlies a different portion of the right lung.

8. The method of claim 7, wherein the step of disposing each said first and second plurality of transducer bands further comprises disposing three generally oval transducer bands above each lung so that a first of said oval transducer bands is positioned above an upper region of its corresponding lung, a second of said oval transducer bands is positioned above a middle region of its corresponding lung, and a third of said oval transducer bands is positioned above a lower region of its corresponding lung.

9. The method of claim 7, wherein the step of disposing each of said first and second plurality of transducer bands further comprises disposing each of said bands near a mid-clavicular line anteriorly and near a mid-scapular line posteriorly.

10. The method of claim 7, wherein the step of disposing said first and second plurality of transducer bands further comprise disposing said first and second plurality of inductive plethysmographic transducer bands in spaced relation about the left and right shoulders, respectively, of the subject.

11. The method of claim 10, further comprising the step of securing said transducer bands to the subject.

12. A non-invasive apparatus for monitoring individual lung function in a subject having a torso and right and left sides of the torso defined on opposite sides of a midsternal line, comprising:
    transducer means adapted for disposition on one only of the right and the left sides of the subject's torso for overlying only a portion of the chest and back of the subject's torso above an individual lung to be monitored, said transducer producing a signal corresponding to movement of the portion therebeneath; and
    means for monitoring the signal produced by said transducer, said signal corresponding to volume changes in the underlying individual lung.

13. The apparatus of claim 12, wherein said transducer means comprises a first inductive plethysmographic transducer comprising a first hemithoracic transducer band for disposition on the right side of the subject's torso for monitoring right lung functions, said apparatus further comprising a second inductive plethysmographic transducer comprising a second hemithoracic transducer band for disposition on the left side of the subject's torso for monitoring left lung functions, each of said first and second transducer bands comprising a continuous loop for coursing, anteriorly, vertically near a right mid-clavicular line and a left mid-clavicular line, respectively, of the subject's torso, then horizontally at a lower right and left rib cage, respectively, and then posteriorly, vertically near a right mid-scapular line and a left mid-scapular line, respectively, of the subject's torso back to a left and a right shoulder, respectively.

14. The apparatus of claim 13, further including means for holding each of said transducer bands in place on the subject.

15. The apparatus of claim 13, wherein said continuous loop is about 2.5 centimeters wide.

16. The apparatus of claim 12, wherein said transducer means comprises at least one inductive plethysmographic transducer.

17. The apparatus of claim 16, wherein said at least one plethysmographic transducer comprises a wire having an inductance, and said means for monitoring comprises means for converting the inductance of the wire of said at least one transducer to a proportional voltage signal, and means connected to said converting means for recording or displaying said voltage signals.

18. The apparatus of claim 17, wherein said converting means comprises an LC oscillator having an inductance element and a frequency to voltage converter connected to said LC oscillator, and wherein said inductive plethysmographic transducer forms the inductance element of said LC oscillator.

19. The apparatus of claim 18, wherein said at least one plethysmographic transducer comprises at least first and second plethysmographic transducers dimensioned for disposition above the left and right lungs of said subject, respectively; wherein said at least one LC oscillator comprises at least a first LC oscillator for said first transducer and at least a second LC oscillator connected to said second transducer; and wherein said at least one frequency to voltage converter comprises at least a first frequency to voltage converter connected to said first LC oscillator and at least a second frequency to voltage converter connected to said second LC oscillator; and wherein said first inductive plethysmographic transducer forms the inductance element of said first LC oscillator and said second inductive plethysmographic transducer forms the inductance element of said second LC oscillator.

20. The apparatus of claim 19, further comprising first and second calibrating means for calibrating output signals from said first and second plethysmographic transducers connected to said at least first and second frequency to voltage converters, respectively.

21. The apparatus of claim 20, wherein said at least first and second calibrating means include first and second scaling amplifiers, respectively.

22. The apparatus of claim 21, further including a summing means connected to said at least first and second scaling amplifiers for summing the signals therefrom.

23. The apparatus of claim 22, wherein said summing means comprises a microprocessor.

24. The apparatus of claim 22, further including means for recording or displaying an output from said summing means.

25. The apparatus of claim 20, further comprising a summing means connected to said at least first and second calibrating means for summing the signals therefrom.

26. The apparatus of claim 25, wherein said summing means comprises a summing amplifier.

27. The apparatus of claim 25, wherein said summing means comprises a microprocessor.

28. The apparatus of claim 25, further including means for recording or displaying an output from said summing means.

29. The apparatus of claim 12, wherein said transducer comprises a first inductive plethysmographic transducer comprising a first plurality of inductive plethysmographic transducer bands for positioning above a left lung of the subject, each of said bands of said first plurality of bands overlying a different portion of the left lung, said apparatus further comprising a second inductive plethysmographic transducer comprising a second plurality of inductive plethysmographic transducer bands for positioning above a right lung of the subject, each of said bands of said second plurality of bands overlying a different portion of the right lung.

30. The apparatus of claim 29, wherein each of said first and second plurality of transducer bands comprise three generally oval transducer bands, a first adapted to be positioned above an upper region of a corresponding lung, a second adapted to be positioned above a middle region of said corresponding lung, and a third adapted to be positioned above a lower region of said corresponding lung of said subject.

31. The apparatus of claim 30, further including means for securing said bands to said subject.

32. The apparatus of claim 29, further including means for securing said bands to said subject.

33. A non-invasive method for monitoring individual lung function in a subject having a torso and right and left sides of the torso defined on opposite sides of a midsternal line, comprising the steps of:
 a. disposing a transducer on the subject's torso, said transducer being disposed on one only of the right and the left sides of the subject's torso for overlying only a portion of the chest and back of the subject's torso above an individual lung to be monitored, said transducer comprising a stretchable conductor whose inductance changes as it stretches in response to movements of the portion therebeneath;
 b. converting the inductance of said conductor to a proportional voltage signal; and
 c. recording or displaying said voltage signal, said voltage signal being indicative of the individual lung function.

34. The non-invasive method of claim 33, wherein said converting step (b) comprises incorporating the conductor as an inductance element of an LC oscillator and converting frequency changes of said LC oscillator to corresponding voltage signal changes.

35. The method of claim 33, wherein said transducer comprises a first transducer, said stretchable conductor comprises a first stretchable conductor, and said first transducer disposing step further comprises disposing the first transducer above a left lung of the subject, said method further comprising the steps of disposing a second transducer having a second stretchable conductor above a right lung of the subject so that an inductance of the second conductor changes as it stretches in response to movements of the portion therebeneath, and converting the inductance of the second conductor to a proportional voltage signal indicative of the function of the right lung, wherein each of said converting steps comprises incorporating the respective conductors as inductance elements of respective LC oscillators and converting frequency changes of said LC oscillators to corresponding voltage signal changes, and said method further comprising a step of calibrating said voltage signals from said first and second transducers to reflect the relative contributions of the left and right lungs to total lung ventilation.

36. The method of claim 35, further comprising a step of summing said voltage signals which have been calibrated.

37. The method of claim 36, further comprising steps of:
 measuring an absolute total lung volume using spirometry; and
 calibrating at least one of said voltage signals until the summed calibrated voltage signal equals said absolute total lung volume as measured by spirometry, whereby said summed calibrated voltage signal is indicative of said absolute total lung volume.

38. The method of claim 37, further comprising a step of recording or displaying said summed calibrated voltage signal.

39. The method of claim 35, further comprising a step of recording or displaying said calibrated voltage signals.

* * * * *

UNITED STATES PATENT AND TRADEMARK OFFICE
CERTIFICATE OF CORRECTION

PATENT NO. : 5,159,935
DATED : November 3, 1992
INVENTOR(S) : Marvin A. Sackner and Jonathan D. Sackner It is certified that error appears in the above-identified patent and that said Letters Patent is hereby corrected as shown below:

Title page:

In the "Inventors:" field replace "Joathan" with --Jonathan--.

In column 1, line 17, after "or" add --pneumotachygraphs, respectively. Gaensler, E.A.: Bronchospirometry--.

In column 8, line 25, after "respectively" add --,--.

Signed and Sealed this

Thirteenth Day of April, 1993

Attest:

STEPHEN G. KUNIN

*Attesting Officer*   *Acting Commissioner of Patents and Trademarks*